United States Patent [19]

Esanu et al.

[11] Patent Number: 5,168,098
[45] Date of Patent: Dec. 1, 1992

[54] PYRROLO-PYRIDINE DERIVATIVES AND THERAPEUTIC COMPOSITIONS CONTAINING THEM

[75] Inventors: André Esanu, Paris; Pierre Braquet, Garches, both of France

[73] Assignee: Societe de Conseils de Recherches et d'Applications Scientifiques (S.C.R.A.S.), France

[21] Appl. No.: 708,675

[22] Filed: May 31, 1991

[30] Foreign Application Priority Data

Jun. 9, 1990 [GB] United Kingdom ............... 9012926

[51] Int. Cl.⁵ .................. A61K 31/435; C07D 471/04
[52] U.S. Cl. .................................. 514/300; 546/113
[58] Field of Search ........................ 546/113; 514/300

[56] References Cited

U.S. PATENT DOCUMENTS 2,767,191 10/1956 Wright, Jr. et al. ............... 546/113
4,206,117 6/1980 Von Phillipsborn et al. ...... 546/113

OTHER PUBLICATIONS

Koruncev et al., Farm. Glas., 39(9), pp. 265-274 (1983); Chemical Abstracts, 101(9): 72638r (1983).

Primary Examiner—Bernard Dentz
Attorney, Agent, or Firm—Lucas & Just

[57] ABSTRACT

The invention relates to pyrrolo-pyridine derivatives of the formula:

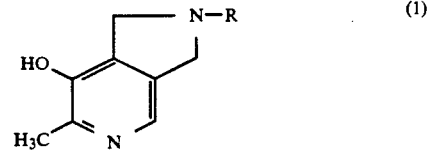

wherein R represents a phenyl group, optionally substituted by one or more of various groups and therapeutically acceptable salts of these compounds, to a preparation process of the same comprising reacting, in an inert atmosphere and in a protic solvent, the 2-methyl 3-hydroxy 4,5-diboromomethyl pyridine, on a stoichiometric excess of the compound of the formula $NH_2$-R.

The invention relates also to therapeutic compositions containing said derivatives as active ingredient.

The compounds according to the invention have antiallergic activity.

2 Claims, No Drawings

PYRROLO-PYRIDINE DERIVATIVES AND THERAPEUTIC COMPOSITIONS CONTAINING THEM

The invention relates to pyrrolo-pyridine derivatives, to a process for their preparation and to therapeutic compositions containing them.

The invention relates more particularly to pyrrolo-pyridine derivatives of the formula:

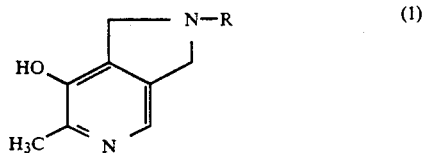

wherein R represents a phenyl group, optionally substituted by one or more of the groups selected from chlorine or fluorine atoms; carboxy, hydroxy or cyano groups; straight chain or branched chain alkyl groups having up to 10 carbon atoms and being unsubstituted or substituted by one or more hydroxy and/or cyano and/or carboxy groups; alkoxy groups having up to 10 carbon atoms; alkylcarbonyl groups having up to 8 carbon atoms; and alkoxycarbonyl groups having up to 8 carbon atoms, and therapeutically acceptable salts thereof.

The invention also relates to a process for the preparation of pyrrolo-pyridine derivatives of the formula (1) as above defined, the process comprising reacting, in an inert atmosphere, the 2-methyl 3-hydroxy 4,5-dibromomethyl pyridine, with a stoichiometric excess of the compound of the formula $NH_2$-R wherein R is as above defined, in a protic solvent, at a temperature of from room temperature to the boiling point of the reacting mixture.

The 2-methyl 3-hydroxy 4,5-dibromomethyl pyridine hydrobromide, used as the starting compound in the process of the invention, may be readily prepared as follows: in a two liter-reactor fitted with appropriate means and placed under nitrogen circulation, 33 g (0.16 mol) of pyridoxine hydrochloride and 460 ml of hydrobromic acid (47% by volume) were poured. The mixture was slowly warmed to reflux temperature and reflux was maintained for about 15 mn. After cooling to room temperature, the resulting compound was filtered off, washed three times with icy-water then once with acetone and dried under reduced pressure on sulfuric acid atmosphere to yield 43.8 g (72.6%) of 2-methyl 3-hydroxy 4,5-dibromomethyl pyridine hydrobromide.

6-methyl-2-(substituted phenyl)-pyrrolo [3,4-c]pyridines are known from Form Glas., 1983, 39 (9). The compounds there disclosed have various substituents in the 7-position but have only the trifluoromethyl group as a substituent of the 2-phenyl group. They have antimicrobial activities. By contrast, as defined hereinunder, the compounds of the invention have a 7-hydroxy substituent and do not have a trifluoromethyl substituent on the 2-phenyl group. Moreover, they have antiallergic activity but no antimicrobial activity.

To date, in the allergy field, two types of antiallergic compounds may be found: symptomatic compounds and compounds blocking mechanisms in the first stages of the allergy reaction; the mainly-used compounds of this category, are sodium cromoglycate (Lomusol ®) which may be administered only by aerosol and not P.O, in contrast with ketotifen (Zaditen ®) which may be administered P.O. but, due to its aspecificity, presents secondary effects which in some cases may not be accepted.

The compounds of the invention have shown antiallergic activity: pharmacological experiments (such as the Passive Cutaneous Anaphylaxy (PCA) test as described in the pharmacology part) have shown that they inhibited the degranulation, and complementary studies have shown also that, in contradistinction to ketotifen, they had no significant effect as anti-PAF, antileukotriene antihistaminic or anticholinergic agents, so they did not act on mediators; these results indicated that they operated above mediators, at the beginning of the allergy reaction, and act at a stage prior to the stages at which the usual antiallergics act.

The invention further relates to therapeutic compositions comprising a pyrrolo-pyridine derivative of the formula (1) as above defined or therapeutically acceptable salts thereof in admixture with a therapeutically acceptable diluent or carrier.

The invention will be better understood from the description of the following examples.

EXAMPLE 1

2-(phenyl) 6-methyl 7-hydroxy 1,3-dihydro pyrrolo [3,4-c]pyridine

R = phenyl

In a two liter-reactor fitted with appropriate means and placed under nitrogen circulation, were poured 37.6 g (0.10 mol) of 2-methyl 3-hydroxy 4,5-dibromomethyl pyridine hydrobromide, 21.4 g (0.23 mol) of aniline and 500 ml of toluene. The mixture was slowly warmed to reflux temperature and reflux was maintained for two hours. Then the suspension was stirred overnight. The thus obtained compound was filtered off, washed with diethyl-ether then, treated with 500 ml of a mixture of water/diethyl-ether (80/20 by volume). Thereafter 100 ml of a 5M sodium hydroxide solution was added and the pH was then acidified to pH 5 by addition of acetic acid. After filtration, the recovered compound was successively washed with water, ethanol, diethyl-ether and then dried. The residue thus obtained was treated by 300 ml of a methanol/chloroform mixture (2/1 by volume) and the mixture was refluxed. After cooling, the resulting compound was filtered off and washed with diethyl-ether.

Yield was 16.6 g (73.4%) of a beige powder melting at 270° C. (Tottoli). The elemental analysis showed a good correspondence with the formula $C_{14}H_{14}N_2O$ (molecular weight 226.28).

$^1$H-NMR (CF$_3$COOD/TMS) δ: 2.90 (s. CH$_3$), 5.60 (s. CH$_2$), 5.68 (s. CH$_2$), 7.70 (s. 5H), 8.43 (s. 1H)

The following compounds have been prepared as described in example 1, using the appropriate $NH_2$-R reagent.

EXAMPLE 2

2-(3-methylphenyl) 6-methyl 7-hydroxy 1,3-dihydro pyrrolo [3,4-c]pyridine

R = 3-methylphenyl

Cream-white powder melting at 268°–270° C. (Tottoli). Elemental analysis showed a good correspondence with the formula $C_{15}H_{16}N_2O$ (molecular weight 240.30).

¹H-NMR (CF₃COOD/TMS) δ: 2.8 (s. CH₃), 3.1 (s. CH₃), 5.7 (s. 2CH₂), 7.6 (s. 4H), 8.2 (s. 1H)

EXAMPLE 3

2-(4-isopropylphenyl) 6-methyl 7-hydroxy 1,3-dihydro pyrrolo [3,4-c]pyridine

R=4-isopropylphenyl

Yellow powder melting at a temperature above 300° C. (Tottoli). Elemental analysis showed a good correspondence with the formula $C_{17}H_{20}N_2O$ (molecular weight 268.36).

¹H-NMR (DMSO/TMS) δ: 1.2 (d. 2CH₃), 2.7 (s. CH₃), 3.4 (m. 1H), 5.4 (s. 2CH₂), 7.4 (s. 4H), 8.2 (s. 1H)

EXAMPLE 4

2-(4-terbutylphenyl) 6-methyl 7-hydroxy 1,3-dihydro pyrrolo [3,4-c]pyridine

R=4-terbutylphenyl

Yellow powder melting at 270° C. (Tottoli). Elemental analysis showed a good correspondence with the formula $C_{18}H_{22}N_2O$. HCl (molecular weight 318.85).

¹H-NMR (DMSO/TMS) δ: 1.26 (s. 3CH₃), 2.43 (s. CH₃), 4.57 (s. 2CH₂), 6.54–6.63 (d. 2H) 7.25–7.33 (d. 2H), 8.1 (s. 1H)

EXAMPLE 5

2-(3-hydroxyethylene phenyl) 6-methyl 7-hydroxy 1,3-dihydro pyrrolo [3,4-c]pyridine R=3-hydroxyethylenephenyl Pale yellow powder melting at 256°–257° C. (Tottoli). Elemental analysis showed a good correspondence with the formula $C_{16}H_{18}N_2O_2$. HCl (molecular weight 306.80).

¹H-NMR (CF₃COOD/TMS) δ: 2.8 (s. CH₃), 3.1 (d. CH₂), 4.1 (t. CH₂), 5.3 (s. 2CH₂), 7.2–7.5 (m. 4H) 8.3 (s. 1H)

EXAMPLE 6

2-(4-cyanomethylenephenyl) 6-methyl 7-hydroxy 1,3-dihydro pyrrolo [3,4-c]pyridine R=4-cyanomethylenephenyl Yellow powder melting at 211°–212° C. (Tottoli). Elemental analysis showed a good correspondence with the formula $C_{16}H_{15}N_3O$ (molecular weight 265.32).

¹H-NMR (DMSO/TMS) δ: 2.8 (s. CH₃), 3.9 (s. CH₂), 5.2 (s. 2CH₂), 7.3 (s. 4H), 8.3 (s. 1H)

EXAMPLE 7

2-(4-carboxymethylenephenyl) 6-methyl 7-hydroxy 1,3-dihydro pyrrolo [3,4-c]pyridine R=4-carboxymethylenephenyl Beige powder melting at 261°–264° C. (Tottoli). Elemental analysis showed a good correspondence with the formula $C_{16}H_{16}N_2O_3$ (molecular weight 284.32).

¹H-NMR (DMSO/TMS) δ: 2.4 (s. CH₃), 3.9 (s. CH₂), 5.1 (s. 2CH₂), 7.2–7.3 (m. 4H), 8.2 (s. 1H)

EXAMPLE 8

2-(3-methoxyphenyl) 6-methyl 7-hydroxy 1,3-dihydro pyrrolo [3,4-c]pyridine

R=3-methoxyphenyl

Pale yellow powder melting at 251°–252° C. (Tottoli). Elemental analysis showed a good correspondence with the formula $C_{15}H_{16}N_2O_2$ (molecular weight 256.31).

¹H-NMR (DMSO/TMS) δ: 2.8 (s. CH₃), 4.1 (s. OCH₃), 6.2 (s. 2CH₂), 7.1–7.5 (m. 4H), 8.0 (s. 1H)

EXAMPLE 9

2-(4-ethoxyphenyl) 6-methyl 7-hydroxy 1,3-dihydro pyrrolo [3,4-c]pyridine

R=4-ethoxyphenyl

Pale beige powder melting at 243°–244° C. (Tottoli). Elemental analysis showed a good correspondence with the formula $C_{16}H_{18}N_2O_2$. HCl (molecular weight 306.79).

¹H-NMR (DMSO/TMS) δ: 1.2 (t. CH₃), 2.5 (s. CH₃), 4.1 (q. CH₂), 5.6 (s. 2CH₂), 7.6 (s. 4H), 8.22 (s. 1H)

EXAMPLE 10

2-(2,4-dimethoxyphenyl) 6-methyl 7-hydroxy 1,3-dihydro pyrrolo [3,4-c]pyridine

R=2,4-dimethoxyphenyl

Beige powder melting at 216° C. (Tottoli). Elemental analysis showed a good correspondence with the formula $C_{16}H_{18}N_2O_3$ (molecular weight 286.33).

¹H-NMR (DMSO/TMS) δ: 2.35 (s. CH₃), 3.7 (s. OCH₃), 3.8 (s. OCH₃), 4.48 (s. 2CH₂), 6.3–6.8 (m. 3H) 7.93 (s. 1H)

EXAMPLE 11

2-(3,4-dimethoxyphenyl) 6-methyl 7-hydroxy 1,3-dihydro pyrrolo [3,4-c]pyridine

R=3,4-dimethoxyphenyl

Yellow powder melting at 265° C. (Tottoli). Elemental analysis showed a good correspondence with the formula $C_{16}H_{18}N_2O_3$. HBr (molecular weight 367.24).

¹H-NMR (CF₃COOD/TMS) δ: 2.9 (s. CH₃), 4.0 (s. 2OCH₃), 5.5–6.5 (d. 2CH₂), 7.15–7.55 (m. 3H), 8.45 (s. 1H)

EXAMPLE 12

2-(3,4,5-trimethoxyphenyl) 6-methyl 7-hydroxy 1,3-dihydro pyrrolo [3,4-c]pyridine R=3,4,5-trimethoxyphenyl Yellow powder melting at 220° C. (Tottoli). Elemental analysis showed a good correspondence with the formula $C_{17}H_{20}N_2O_4$ (molecular weight 316.36).

¹H-NMR (CDCl₃/TMS) δ: 2.4 (s. CH₃), 3.67 (s. OCH₃), 3.73 (s. 2OCH₃), 4.55 (s. 2CH₂), 5.72 (s. 3H) 8.0 (s. 1H)

EXAMPLE 13

2-(4-chlorophenyl) 6-methyl 7-hydroxy 1,3-dihydro pyrrolo [3,4-c]pyridine

R=4-chlorophenyl

Cream-white powder melting at 256°–258° C. (Tottoli). Elemental analysis showed a good correspondence with the formula $C_{14}H_{13}ClN_2O$ (molecular weight 260.72).

¹H-NMR (DMSO/TMS) δ: 2.8 (s. CH₃), 5.2 (s. 2CH₂), 7.3 (s. 4H), 8.3 (s. 1H)

EXAMPLE 14

2-(2,4-difluorophenyl) 6-methyl 7-hydroxy 1,3-dihydro pyrrolo [3,4-c]pyridine

R=2,4-difluorophenyl

Pale beige powder melting at 279° C. (Tottoli). Elemental analysis showed a good correspondence with the formula $C_{14}H_{12}F_2N_2O$ (molecular weight 262.26).

$^1$H-NMR (DMSO/TMS) δ: 2.6 (s. CH$_3$), 4.83 (s. 2CH$_2$), 6.8–7.2 (m. 3H), 8.45 (s. 1H)

EXAMPLE 15

2-(2,6-dichlorophenyl) 6-methyl 7-hydroxy 1,3-dihydro pyrrolo [3,4-c]pyridine

R = 2,6-dichlorophenyl

Cream white powder melting at 262° C. (Tottoli). Elemental analysis showed a good correspondence with the formula C$_{14}$H$_{12}$Cl$_2$N$_2$O (molecular weight 295.17).

$^1$H-NMR (CF$_3$COOD/TMS) δ: 2.92 (s. CH$_3$), 5.9 (s. 2CH$_2$), 7.72 (s. 3H), 8.45 (s. 1H)

EXAMPLE 16

2-(3-hydroxyphenyl) 6-methyl 7-hydroxy 1,3-dihydro pyrrolo [3,4-c]pyridine

R = 3-hydroxyphenyl

Yellow powder melting at 306° C. (Tottoli). Elemental analysis showed a good correspondence with the formula C$_{14}$H$_{14}$N$_2$O$_2$. HBr (molecular weight 323.19).

$^1$H-NMR (DMSO/TMS) δ: 2.65 (s. CH$_3$), 4.72 (s. 2CH$_2$), 6.0–6.4 (m. 3H), 6.9–7.3 (m. 1H), 8.51 (s. 1H)

EXAMPLE 17

2-(4-hydroxyphenyl) 6-methyl 7-hydroxy 1,3-dihydro pyrrolo [3,4-c]pyridine

R = 4-hydroxyphenyl

Yellow powder melting at a temperature above 260° C. Elemental analysis showed a good correspondence with the formula C$_{14}$H$_{14}$N$_2$O$_2$. HBr (molecular weight 323.19).

$^1$H-NMR (DMSO/TMS) δ: 2.57 (s. CH$_3$), 4.68 (s. 2CH$_2$), 6.3–6.8 (m. 4H), 8.38 (s. 1H)

EXAMPLE 18

2-(2,4-dihydroxyphenyl) 6-methyl 7-hydroxy 1,3-dihydro pyrrolo [3,4-c]pyridine

R = 2,4-dihydroxyphenyl

Green-yellow powder melting at a temperature above 260° C. (Tottoli). Elemental analysis showed a good correspondence with the formula C$_{14}$H$_{14}$N$_2$O$_3$ (molecular weight 258.27).

$^1$H-NMR (DMSO/TMS) δ: 2.38 (s. CH$_3$), 4.43 (s. 2CH$_2$), 6.1–6.8 (m. 3H), 7.92 (s. 1H)

EXAMPLE 19

2-(2,4,6-trihydroxyphenyl) 6-methyl 7-hydroxy 1,3-dihydro pyrrolo [3,4-c]pyridine R = 2,4,6-trihydroxyphenyl Yellow powder melting at 290°–291° C. Elemental analysis showed a good correspondence with the formula C$_{14}$H$_{14}$N$_2$O$_4$ (molecular weight 274.27).

$^1$H-NMR (DMSO/TMS) δ: 2.2 (s. CH$_3$), 5.1 (s. 2CH$_2$), 6.2 (s. 1H), 6.7 (s. 1H), 8.1 (s. 1H)

EXAMPLE 20

2-[(4-hydroxy 2-methoxy) phenyl]6-methyl 7-hydroxy 1,3-dihydro pyrrolo [3,4-c]pyridine R = (4-hydroxy 2-methoxy)phenyl Yellow powder melting at a temperature above 260° C. (Tottoli). Elemental analysis showed a good correspondence with the formula C$_{15}$H$_{16}$N$_2$O$_{10}$. HCl (molecular weight 308.76).

$^1$H-NMR (DMSO/TMS) δ: 2.62 (s. CH$_3$), 3.7 (s. OCH$_3$), 4.1–4.3 (m. 2CH$_2$), 6.3–6.9 (m. 3H), 8.27 (s. 1H)

EXAMPLE 21

2-[(4-hydroxy 2-ethoxy) phenyl]6-methyl 7-hydroxy 1,3-dihydro pyrrolo [3,4-c]pyridine R = (4-hydroxy 2-ethoxy)phenyl White powder melting at 269°–270° C. (Tottoli). Elemental analysis showed a good correspondence with the formula C$_{16}$H$_{18}$N$_2$O$_3$. HCl (molecular weight 322.79).

$^1$H-NMR (CF$_3$COOD/TMS) δ: 1.3 (t. CH$_3$), 2.5 (s. CH$_3$), 4.1 (q. CH$_2$), 5.6 (s. CH$_2$), 7.2–7.6 (m. 3H) 8.2 (s. 1H)

EXAMPLE 22

2-(3-carboxyphenyl) 6-methyl 7-hydroxy 1,3-dihydro pyrrolo [3,4-c]pyridine

R = 3-carboxyphenyl

Yellow powder melting at 286° C. (Tottoli). Elemental analysis showed a good correspondence with the formula C$_{15}$H$_{14}$N$_2$O$_3$. HCl$_{0.5}$H$_2$O (molecular weight 315.75).

$^1$H-NMR (DMSO/TMS) δ: 2.61 (s. CH$_3$), 4.3–4.6 (m. COOH), 4.73 (m. 2CH$_2$), 6.8–7.4 (m. 4H), 8.3 (s. 1H)

EXAMPLE 23

2-(4-carboxyphenyl) 6-methyl 7-hydroxy 1,3-dihydro pyrrolo [3,4-c]pyridine

R = 4-carboxyphenyl

Yellow powder melting at a temperature above 300° C. (Tottoli). Elemental analysis showed a good correspondence with the formula C$_{15}$H$_{14}$N$_2$O$_3$. HCl (molecular weight 306.75).

$^1$H-NMR (CF$_3$COOD/TMS) δ: 2.9 (s. CH$_3$), 5.35 (m. 2CH$_2$), 7.4 (s. 1H), 8.2–8.5 (m. 4H)

EXAMPLE 24

2-[(2methoxy 5-carboxy) phenyl]6-methyl 7-hydroxy 1,3-dihydro pyrrolo [3,4-c]pyridine R = (2-methoxy 5-carboxy)phenyl Yellow powder melting at 277° C. (Tottoli). Elemental analysis showed a good correspondence with the formula C$_{16}$H$_{16}$N$_2$O$_4$. HBr (molecular weight 381.22).

$^1$H-NMR (DMSO/TMS) δ: 2.62 (s. CH$_3$), 3.93 (s. OCH$_3$), 4.74 (s. 2CH$_2$), 7.0–7.5 (m. 3H), 8.4 (s. 1H)

EXAMPLE 25

2-(3-cyanophenyl) 6-methyl 7-hydroxy 1,3-dihydro pyrrolo [3,4-c]pyridine

R = 3-cyanophenyl

Cream-white powder melting at a temperature above 310° C. (Tottoli). Elemental analysis showed a good correspondence with the formula C$_{15}$H$_{13}$N$_3$O (molecular weight 251.29).

$^1$H-NMR (CF$_3$COOD/TMS) δ: 2.87 (s. CH$_3$), 5.1–5.3 (m. 2CH$_2$), 7.2–7.6 (m. 4H), 8.32 (s. 1H)

EXAMPLE 26

2-(4-cyanophenyl) 6-methyl 7-hydroxy 1,3-dihydro pyrrolo [3,4-c]pyridine

R = 4-cyanophenyl

Pale beige powder melting at a temperature above 310° C. (Tottoli). Elemental analysis showed a good correspondence with the formula C$_{15}$H$_{13}$N$_3$O (molecular weight 251.29).

¹H-NMR (CF₃COOD/TMS) δ: 2.9 (s. CH₃), 5.2 (m. 2CH₂), 7.3–7.6 (m. 4H), 8.2 (s. 1H)

EXAMPLE 27

2-(4-methylcarbonylphenyl) 6-methyl 7-hydroxy 1,3-dihydro pyrrolo [3,4-c]pyridine R=4-methylcarbonylphenyl Pale yellow powder melting at 247°–249° C. (Tottoli). Elemental analysis showed a good correspondence with the formula C₁₆H₁₆N₂O₂. HCl (molecular weight 304.78).

¹H-NMR (DMSO/TMS) δ: 2.7 (s. CH₃), 3.8 (s. CH₃), 5.1 (s. 2CH₂), 7.1–7.4 (m. 4H), 8.1 (s. 1H)

EXAMPLE 28

2-(4-ethylcarbonylphenyl) 6-methyl 7-hydroxy 1,3-dihydro pyrrolo [3,4-c]pyridine R=4-ethylcarbonylphenyl Yellow powder melting at 288°–289° C. (Tottoli). Elemental analysis showed a good correspondence with the formula C₁₇H₁₈N₂O₂ (molecular weight 282.34).

¹H-NMR (DMSO/TMS) δ: 1.2 (t. CH₃), 2.7 (s. CH₃), 4.1 (q. CH₂), 5.2 (s. 2CH₂), 7.3 (s. 4H), 8.1 (s. 1H)

EXAMPLE 29

2-(4-methoxycarbonylphenyl) 6-methyl 7-hydroxy 1,3-dihydro pyrrolo [3,4-c]pyridine R=4-methoxycarbonylphenyl Beige powder melting at 233°–235° C. (Tottoli). Elemental analysis showed a good correspondence with the formula C₁₆H₁₆N₂O₃ (molecular weight 284.31).

¹H-NMR (DMSO/TMS) δ: 2.8 (s. CH₃), 3.6 (s. CH₃), 5.1 (s. 2CH₂), 7.1–7.5 (m. 4H), 8.2 (s. 1H)

EXAMPLE 30

2-(4-ethoxycarbonylphenyl) 6-methyl 7-hydroxy 1,3-dihydro pyrrolo [3,4-c]pyridine R=4-ethoxycarbonylphenyl Pale beige powder melting at 226°–227° C. (Tottoli). Elemental analysis showed a good correspondence with the formula C₁₇H₁₈N₂O₃ (molecular weight 298.34).

¹H-NMR (DMSO/TMS) δ: 1.3 (t. CH₃), 2.8 (s. CH₃), 4.3 (q. CH₂), 5.2 (s. 2CH₂), 7.1–7.4 (m. 4H) 8.4 (s. 1H)

TOXICITY

For none of the compounds of the invention, per os administration of 1000 mg/kg to mice resulted in any death.

PHARMACOLOGY

The pharmaceutical interest of the compounds of the invention has been established, with ketotifen as the reference compound, by the following pharmaceutical experiments: test of Passive Cutaneous Anaphylaxy (PCA) on the rat associated with hyperpermeability to histamine.

This experiment was conducted as described in 'Fiche Technique' No. 48 of J. Pharm. Paris 1979 10 (1) pages 69–72 (adaptation of the method of BITTEAU E. and HERTZ F.) The method is summarized as follows:

Twelve batches of each 8 male Sprague Dawley rats (180–200 g)—one for the control, one for the reference compound, at the dose of 1 mg/kg, and one for each example compounds, at the dose of 50 mg/kg—have been used.

In two sites of the back, previously shaved, were made two injections of an homologous immune-serum (0.1 ml) diluted for a quater.

48 hours later, the rats received an intravenous injection of 1 ml of a mixture of ovalbumine (0.5%), and Evans blue (0.5%), in physiologic serum. As a consequence, the formation of the antigen-antibody complex induced the exudation of plasmatic proteins and the formation of cutaneous wheals, this phenomenon being quantified by measuring their surface and their coloration, (after extracting for 24 hours in a formamide solution at 65° C.), the optical density of the supernatant was determined at 620 nm by a spectrophotometer.

The animals were kept fasting for 18 hours before injection of antigen. The products were administered PO one hour before the administration of colorant.

Just before the IV injection of colorant, all animals received two intradermal injections, in two sites of the back, of histamine chlorhydrate (50 mcg/0.1 ml), opposed to the injections of the immune-serum.

30 minutes later, the induced wheals were treated like the wheals obtained with immune-serum.

The experimental results are summarized in the following table.

POSOLOGY

In human therapy usual doses per os administration, are 1 to 10 mg per diem, in tablets, gelatin capsules or in suspension, for at least month. For IV route, the usual doses are from 0.5 to 2 mg per diem.

|  | immune-serum wheals | | histamine wheals | |
|---|---|---|---|---|
|  | area mm² | coloration (DO) | area mm² | coloration (DO) |
| control | 113.2 ± 8.47 | 0.634 ± 0.0774 | 125.2 ± 6.87 | 0.959 ± 0.0858 |
| Ketotifen | 73.8 ± 7.51 −34.8*** | 0.347 ± 0.0646 −45.3*** | 78.6 ± 6.67 −37.2*** | 0.333 ± 0.0672 −65.3*** |
| ex 1 | 58.6 ± 4.15 −48.2*** | 0.314 ± 0.0348 −50.5*** | 103.2 ± 4.18 −17.6 NS | 0.777 ± 0.0677 −19 NS |
| ex 4 | 70.2 ± 8.9 −38*** | 0.353 ± 0.0694 −44.3*** | 110 ± 5.75 −12.1 NS | 0.975 ± 0.1151 +1.7 NS |
| ex 9 | 58.8 ± 6.2 −48.1*** | 0.304 ± 0.0436 −52*** | 116.2 ± 5.66 −7 NS | 0.868 ± 0.0884 −9.5 NS |
| ex 11 | 53.8 ± 3.3 −52.5*** | 0.284 ± 0.0421 −55.2*** | 117.7 ± 6.23 −6 NS | 0.826 ± 0.0912 −13.9 NS |
| ex 15 | 79.3 ± 7.54 −30** | 0.391 ± 0.059 −38.3*** | 118.8 ± 9.35 −5 NS | 0.791 ± 0.093 −18 NS |
| ex 17 | 62.2 ± 5.77 −45** | 0.337 ± 0.0412 −47** | 109.8 ± 6.39 −12 NS | 0.820 ± 0.095 −14.5 NS |
| ex 20 | 67.8 ± 7.38 | 0.391 ± 0.0723 | 125.1 ± 6.95 | 0.912 ± 0.078 |

-continued

| | immune-serum wheals | | histamine wheals | |
|---|---|---|---|---|
| | area mm$^2$ | coloration (DO) | area mm$^2$ | coloration (DO) |
| | −40** | −38.3** | 0 NS | −5 NS |
| ex 22 | 71.3 ± 4.91 | 0.398 ± 0.0269 | 121.2 ± 7.17 | 0.854 ± 0.092 |
| | −37*** | −37.2*** | −3 NS | −11 NS |
| ex 26 | 64.7 ± 5.6 | 0.384 ± 0.065 | 119.2 ± 5.53 | 0.803 ± 0.106 |
| | −43** | −39** | −5 NS | −16 NS |
| ex 29 | 73.6 ± 7.1 | 0.398 ± 0.044 | 112.7 ± 7.26 | 0.896 ± 0.835 |
| | −35** | −37** | −10 NS | −6.5 NS |

NS: not significant
*significant
**very significant
***highly significant

We claim:
1. Pyrrolo-pyridine derivatives of the formula:

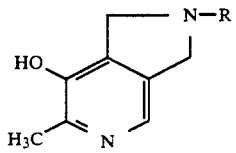
(1)

wherein R represents a phenyl group, optionally substituted by at least one substituent selected from the group consisting of: chlorine and fluorine atoms; carboxy, hydroxy or cyano groups; straight chain or branched chain alkyl groups having up to 10 carbon atoms and being unsubstituted or substituted by one or more hydroxy and/or cyano and/or carboxy groups; alkoxy groups having up to 10 carbon atoms; alkylcarbonyl groups having up to 8 carbon atoms; and alkoxycarbonyl groups having up to 8 carbon atoms, and therapeutically acceptable salts thereof.

2. Therapeutic compositions comprising an admixture of a therapeutically acceptable diluent or carrier with at least one pyrrolo-pyridine derivative of the formula:

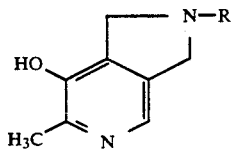
(1)

wherein R represents a phenyl group, optionally substituted by at least one substituent selected from the group consisting of: chlorine and fluorine atoms; carboxy, hydroxy or cyano groups; straight chain or branched chain alkyl groups having up to 10 carbon atoms and being unsubstituted or substituted by one or more hydroxy and/or cyano and/or carboxy groups; alkoxy groups having up to 10 carbon atoms; alkylcarbonyl groups having up to 8 carbon atoms; and alkoxycarbonyl groups having up to 8 carbon atoms, and therapeutically acceptable salts thereof.

* * * * *